(12) United States Patent
Page et al.

(10) Patent No.: US 7,267,817 B2
(45) Date of Patent: Sep. 11, 2007

(54) METHOD FOR IMPROVING OXYGEN TRANSPORT BY STORED RED BLOOD CELLS

(75) Inventors: Thomas C. Page, Watertown, MA (US); William R. Light, Natick, MA (US); Edward E. Jacobs, Jr., Lexington, MA (US)

(73) Assignee: Biopure Corporation, Cambridge, MA (US)

( * ) Notice: Subject to any disclaimer, the term of this patent is extended or adjusted under 35 U.S.C. 154(b) by 339 days.

(21) Appl. No.: 10/967,475

(22) Filed: Oct. 18, 2004

(65) Prior Publication Data

US 2005/0079162 A1 Apr. 14, 2005

Related U.S. Application Data

(62) Division of application No. 09/950,270, filed on Sep. 10, 2001, now Pat. No. 6,811,778.

(51) Int. Cl.
*A01N 63/00* (2006.01)
*A61K 35/18* (2006.01)
*A61K 38/16* (2006.01)

(52) U.S. Cl. .................. 424/93.73; 424/533; 514/6
(58) Field of Classification Search .................... None
See application file for complete search history.

(56) References Cited

U.S. PATENT DOCUMENTS 5,618,919 A 4/1997 Rausch et al.
5,865,784 A 2/1999 Faithfull et al.

OTHER PUBLICATIONS

Gueye et al., "Influence of human haptoglobin polymorphism on oxidative stress induced by free hemoglobin on red blood cells", Clinical Chemistry and Laboratory Medicine 44 (5) : 542-547 (2006), abstract.*
Chang, T.M.S., "The Use of Modified Hemoglobin as an Oxygen Carrying Blood Substitute," *Transfusion Medicine Reviews*, 3(3):213-218 (1989).
Homer, L.D. et al., "Oxygen Gradients between Red Blood Cells in the Microcirculation[1]," *Hypoxia Between Red Cells*, pp. 308-323 (1981).
Lovric, V.A., "Alterations in Blood Components during Storage and their Clinical Significance," *Anaesthesia and Intensive Care*, 12(3):246-251 (1984).
Marik, P.E. et al., "Effect of Stored-Blood Transfusion on Oxygen Delivery in Patients With Sepsis," *JAMA*, 269(23):3024-3029 (1993).
Masouredis, S.P., "Preservation and clinical use of erythrocytes and whole blood," In *Hematology*, Williams et al., eds. (NY: McGraw Hill), pp. 1529-1549 (1983).
Oudemans-van Straaten, H.M. et al., "Analysis of $P_{50}$ and oxygen transport in patients after cardiac surgery," *Intensive Care Med.*, 22:781-789 (1996).
Page, T.C. et al., "Oxygen Transport by Erythrocyte/Hemoglobin Solution Mixtures in an in Vitro Capillary as a Model of Hemoglobin-Based Oxygen Carrier Performance," *Microvascular Research*, 55:54-64 (1998).
Page, T.C. et al., "Prediction of Microcirculatory Oxygen Transport by Erythocyte/Hemoglobin Solution Mixtures," *Microvascular Research*, 56:113-126 (1998).
Page, T.C. et al., "Experimental and Mathematical Simulation of Oxygen Transport by Hemoglobin-based Blood Substitute," In *Blood Substitutes—Present and Future Perspectives*, E. Tsuchida, ed. pp. 135-145 (1998).
Page, T.C. et al., "Oxygen Transport In 10µm Artificial Capillaries," In *Oxygen Transport to Tissue XXI*, Eke et al., eds. (NY: Kluwer Academic/Plenum Publishers), pp. 715-721 (1999).
Page, T.C. et al., "Experimental and Theoretical Simulation of Oxygen Transport with Erythrocytes and Extracellular Hemoglobin-Based Materials," Presented at ISBS VI, Montreal, Quebec, Canada (Aug. 1996).
Page, T.C. et al., "Experimental and Theoretical Simulation of Oxygen Transport with Erythrocytes and Extracellular Hemoglobin Solutions," Presented at Biomedical Engineering Society, Fall Meeting, Boston, Massachusetts (1995).
Page, T.C. et al., "Experimental Determination of Intraluminal Oxygen Transport by Hemoglobin Based Oxygen Transport by Hemoglobin Based Oxygen Carriers In 10 µm Capillaries," Presented at ISOTT, Budapest, Hungry (1998).
Page, T.C. et al., "Experimental Simulation of Oxygen Transport in 10 µm Capillaries," Presented at ISOTT, Milwaukee (1997).
Page, T.C. et al., "In Vitro model of Microcirculatory Oxygen Transport," Presented at the BMES, Fall Meeting, Tempe, Arizona (1994).

(Continued)

*Primary Examiner*—Sandra E. Saucier
(74) *Attorney, Agent, or Firm*—Hamilton, Brook, Smith & Reynolds, P.C.

(57) ABSTRACT

A method of treatment of a patient includes administering to the patient stored red blood cells and a hemoglobin solution. The stored red blood cells and the hemoglobin solution can be administered to the patient simultaneously. Alternatively, the hemoglobin solution can be administered to the patient prior to administrating the stored red blood cells or the stored red blood cells can be administered to the patient prior to administering the hemoglobin solution. A composition of the invention includes stored red blood cells and a hemoglobin solution.

8 Claims, 5 Drawing Sheets

OTHER PUBLICATIONS

Parris, W.C.W. et al., "The effect of intentional hemodilution on $P_{50}$," *J. Cardiovasc. Surg.*, 29:560-562 (1988).

Standl, T. et al., "Hemodynamics and Oxygen Transport During Complete Isovolemic Hemodilution with a New Ultrapurified Poly-Merized Bovine Hemoglobin Solution in a Dog Model," Paper presented at the Annual Meeting of the American Society of Anesthesiologists in Washington, (1993).

Sugerman, H.J. et al., "The Basis of Defective Oxygen Delivery From Stored Blood," *Surgery, Gynecology & Obstetrics*, pp. 733-741 (1970).

Tsai, A.G. et al., "Local Tissue Oxygenation during Constant Red Blood Cell Flux: A Discrete Source Analysis of Velocity and Hematocrit Changes[1]," *Microvascular Research*, 37:308-322 (1989).

Uehira, A., et al., "Oxygen affinity measurement of preserved blood," *Vox Sanguinis*, 70(suppl. 2), (1996).

Valeri, C.R. et al., "Physiologic Effects of Transfusing Red Blood Cells with High Low Affinity for Oxygen to Passively Hyperventalated Anemic Baboons," *Ann. Surg.*, 181(1):106-113 (1974).

Valeri, C.R. et al., "Therapeutic Effectiveness and Safety of Outdated Human Red Blood Cells Rejuvenated to Improve Oxygen Transport Function, Frozen for About 1.5 Years at 80 C, Washed, and Stored at 4 C for 24 Hours Prior to Rapid Infusion," *Transfusion*, 20(3):263-276 (1980).

Wells, R.M.G. et al., "Changes of Blood Oxygen Affinity in Different CPD Solutions during Liquid Storage," *Transfusion*, 21(6):709-714 (1981).

Standl, T. et al., "Bovine haemoglobin is more potent than autologous red blood cells in restoring muscular tissue oxygenation after profound isovolaemic haemodilution in dogs," *Can J Anaesth* 43(7): 714-23 (1996).

LaMuraglia, G.M. et al., "The reduction of the allogenic transfusion requirement in aortic surgery with a hemoglobin-based solution," *J. Vascular Surgery 31*(2):299-308 (Feb. 2000).

Slanetz, P.J. et al., "Hemoglobin blood substitutes in extended preoperative autologous blood donation: An experimental study," *Surgery 115*(2):246-254 (Feb. 1994).

* cited by examiner

METHOD FOR IMPROVING OXYGEN TRANSPORT BY STORED RED BLOOD CELLS

RELATED APPLICATIONS

This application is a divisional of U.S. application Ser. No. 09/950,270, filed Sep. 10, 2001 now U.S. Pat. No. 6,811,778. The entire teachings of the above application is incorporated herein by reference.

BACKGROUND OF THE INVENTION

Stored blood undergoes a number of deleterious biochemical changes over time, known collectively as "storage lesion." These changes can include microaggregation of cells, hemolysis, vesicle formation, decreased membrane flexibility, decreased stability, and increased hemoglobin-oxygen affinity. The changes reduce the overall benefit of administering stored blood or red blood cell containing blood products to the patient and may even cause deleterious effects when transfused into a patient. For example, increased microaggregate formation and loss of membrane flexibility of the red blood cells may cause blockage of microcirculatory vessels resulting in local ischemia and pulmonary dysfunction.

Additionally, the loss of 2,3-diphosphoglycerate (2,3-DPG) in red blood cells results in substantially increased hemoglobin-$O_2$ affinity. Blood stored for greater than one week shows a significant decrease in 2,3-DPG levels. After two weeks, only about 40% of 2,3-DPG remains and by three weeks only about 10% remains. (S. P. Masouredis, Preservation and Clinical Use of Erythrocytes and Whole Blood, Chapter 164, In: Hemology, $3^{rd}$ edition, Williams, Beutler, Erslev and Lichtman, (eds.) McGraw-Hill, NY, pp. 1529-1549 (1983)). The loss of 2,3-DPG produces a concomitant drop in $P_{50}$. For example, after four weeks of storage in the preservative, citrate phosphate dextrose (CPD), the $P_{50}$ of packed red cells drops to approximately 15 mm Hg (Wells et al., *Transfusion* 21:709-714 (1981)). Since release of oxygen from red blood cells usually is proportional to $P_{50}$, the capacity of stored red blood cells to deliver oxygen also decreases over time.

Storage lesions can cause deleterious changes in oxygen transport by decreasing both convective and diffusive oxygen delivery. Microaggregates and inflexible cells may be caught in microvessels, blocking flow to downstream tissue. Additionally, red blood cells containing hemoglobin with relatively high oxygen affinity have reduced ability to release oxygen to tissue. Stored red blood cells having high affinity for oxygen can "rejuvenate" over time after transfusion into the body. Levels of 2,3-DPG return to 30% to 50% of normal by four hours and to normal levels with approximately twenty-four hours, though this rate can be variable. (Valeri and Hirsch, *J. Lab. Clin. Med.* 73:722-733 (1969); Beutler and Wood, *J. Lab. Clin. Med.* 74:300-304 (1969)). The rate of 2,3-DPG recovery may be dependent upon the metabolic state of the patient. (O'Brien and Watkins, *J. Thor. & Cardiovas. Surg.* 40:611 (1960)). Ironically, stored red blood cells are transfused to meet an acute need, but suffer from acute lesion.

While these cells "rejuvenate" in circulation, regaining flexibility and decreasing oxygen affinity over a period of hours, there is a window of reduced oxygen transport that could adversely affect patients, especially those patients that are critically ill. Furthermore, while young healthy patients may compensate for storage lesion; patients with reduced or absent ability to compensate are put at risk of further injury or reduced efficacy of treatment. Paradoxically, this compensatory response of transfusion of red blood cells having high affinity for oxygen in some cases may cause decreased local oxygenation. (Marik and Sibbald, *JAMA* 269:3024-30 (1993)). Production of microemboli is also part of the storage lesion. Microemboli are known to form in packed red cells during storage and on infusion obstruct the microcirculation, causing damage to pulmonary capillary endothelium and alveolar epithelium (Liu, et al., *Ann. Thorac. Surg.* 54:1196-1202 (1992); Gay, et al., *Trauma* 19:80-84 (1979)).

Fresh red blood cells have been recommended for massive transfusions, transfusions of infants, older patients, and patients with cardiovascular and pulmonary disease (Masouredis, S. P., Preservation and Clinical Use of Blood and Blood Components," In: Hemology, (Williams, W. J., Beutler, E., Erslev, A. J. and Lichtman, M. A. eds.) McGraw-Hill, New York, pp. 1529-1549; Sugarman, H. J., et al. *Surg. Gynecol. Obstet.*, 131:733-741 (1970); Valeri, G. R., et al., *Transfusion* 20:263-276 (1980); Hess, W., *Anaesthetist.*, 36:455-467 (1987)). However, the availability of fresh blood cells often is limited.

Therefore, a need exists for products and methods that improve the oxygen transport and delivery efficiency of stored red blood cells.

SUMMARY OF THE INVENTION

The present invention is drawn to a method of treating a patient, by administering to the patient stored red blood cells and a hemoglobin solution.

In one embodiment the hemoglobin solution is administered to the patient, and thereafter stored red blood cells are administered, wherein the hemoglobin solution comprises polymerized hemoglobin and wherein the stored red blood cells have been stored for greater than about forty-eight hours.

In another embodiment, the method includes administering stored red blood cells to the patient and thereafter administering a hemoglobin solution within about eight hours of administering the stored red blood cells, wherein the hemoglobin solution comprises polymerized hemoglobin and wherein the stored red blood cells have been stored for greater than about forty-eight hours.

The present invention is further drawn to a composition comprising a hemoglobin solution and stored red blood cells, wherein the stored red blood cells have been stored for greater than about forty-eight hours.

As demonstrated herein, although storage of red blood cells over time reduced the rate of oxygen release from red blood cells, administration of a hemoglobin solution in addition to stored red blood cells reversed this effect and restored oxygen delivery potential to stored red blood cells. The resulting mixture behaved more like fresh red blood cells in oxygen release. Surprisingly, this effect was obtained even when as little as about ten percent (10%) of the total hemoglobin administered to the patient was in the form of hemoglobin solution. As a result of the studies described herein, it is believed that addition of hemoglobin solution in conjunction with stored red blood cells will result in a substantial increase in oxygen release over administration of the same total amount of hemoglobin in the form of freshly isolated red blood cells.

The method and compositions of the present invention can restore oxygen delivery capacity of stored red blood cells more rapidly than may otherwise be possible. The present invention can be particularly useful in the treatment of critically ill, infant, and elderly patients. Furthermore, adding hemoglobin and stored red blood cells according to the method of the present invention will cause increased tissue oxygenation despite the presence of microemboli, because the smaller hemoglobin molecules are able to pass through the obstructions and deliver oxygen. The methods and compositions of the present invention improve the oxygen transport and delivery efficiency of stored red blood cells and can extend the useful storage period of stored red blood cells.

DETAILED DESCRIPTION OF THE INVENTION

The method of the present invention includes treating a patient by administering to the patient stored red blood cells and a hemoglobin solution. The term "stored red blood cells" includes red blood cells that have a significantly reduced $P_{50}$ as compared to wild-type hemoglobin or red blood cells, where wild-type hemoglobin has a $P_{50}$ of at least about 25 mm Hg. "$P_{50}$" as defined herein means the partial pressure of oxygen at which 50% of the hemoglobin is bound to oxygen. In one embodiment, the stored red blood cells could be native or fresh blood that naturally, by genetic variation or disease, has a $P_{50}$ significantly less than about 25 mm Hg. An example of stored red blood cells having a reduced $P_{50}$ is blood wherein the $P_{50}$ is equal to or less than about 25 mm Hg, equal to or less than about 15 mm Hg. The stored red blood cells can have a reduced level of 2,3-DPG compared to freshly isolated blood from a healthy individual, resulting in reduced $P_{50}$.

In one embodiment of the invention, the stored red blood cells have been isolated from the donor for at least about forty-eight hours prior to administration to the patient. In another embodiment, the stored red blood cells have been isolated from the donor for at least about seven days prior to administration to the patient. In still another embodiment, the stored red blood cells have been isolated from the donor for at least about thirty-five days. In another embodiment, the stored red blood cells have been isolated from the donor for at least forty-two days prior to administration to the patient by the method of the invention.

The stored red blood cells can be preserved blood. The term "preserved blood," as defined herein, means blood that has been treated for storage and subsequent use by transfusion. Suitable methods for preserving blood are well-known. Examples of suitable physical methods for preserving blood are refrigeration and freezing. An example of a suitable chemical method for preserving blood includes addition of compounds such as acid citrate dextrose (ACD) or citrate phosphate dextrose (CPD). Further, blood solutions can be fortified with components such as adenine, glucose, mannitol, or combinations thereof. Additional examples of methods for preserving blood can be found in U.S. Pat. No. 5,487,971, by Holme et al., the teachings of which are incorporated herein by reference in their entirety.

In another embodiment, the stored red blood cells can be derived from frozen red blood cells. Methods of freezing red blood cells are well-known in the art. Such methods typically include rapid freezing and maintenance at low temperatures, such as in liquid nitrogen or freezing in the presence of a cryo-preservative agent, such as glycerol. Typically, the cryo-preservative is removed from the red blood cells prior to transfusion.

In another embodiment, the stored red blood cells have been treated to remove at least about 80% of leukocytes. Other examples of suitable sources of stored red blood cells include packed red blood cells and washed red blood cells.

"Hemoglobin solution," which is also referred to herein as "hemoglobin-based oxygen carrier" or "HBOC," means a liquid suspension of hemoglobin (cell-free hemoglobin). Hemoglobin suitable for use in the invention can be derived form new, old or outdated blood from humans, and/or other mammalian sources, such as bovine, porcine, ovine or canine sources. In addition, transgenically produced hemoglobin, such as the transgenically produced hemoglobin described in *Bio/Technology*, 12:55-59 (1994) and recombinantly produced hemoglobin described in *Nature*, 356:258-260 (1992), are also suitable for use in a hemoglobin solution as described herein.

Preferably, the hemoglobin is inter- and/or intra-molecularly crosslinked. Optionally, or alternatively, the hemoglobin can be conjugated to another molecule, such as polyethylene glycol or glutaraldehyde . Examples of preferred hemoglobin solutions are described in U.S. Pat. No. 5,618,919, by Rausch et al.; U.S. Pat. No. 5,905,141, by Rausch et al.; U.S. Pat. No. 5,084,558, by Rausch et al.; U.S. Pat. No. 5,296,465, by Rausch et al.; U.S. Pat. No. 5,840,852, by Rausch et al.; U.S. Pat. No. 5,753,616, by Rausch et al.; U.S. Pat. No. 5,895,810, by Light et al.; U.S. Pat. No. 5,691,452, by Gawryl et al.; U.S. Pat. No. 5,691,453 by Wertz et al.; and 5,808,011, by Gawryl et al., the teachings all of which are incorporated herein by reference in their entirety. The hemoglobin can have a $P_{50}$ of about 25 mm Hg, or a $P_{50}$ of greater than 25 mm Hg. In a particular embodiment, the hemoglobin has a $P_{50}$ of at least about 38 mm Hg.

In one embodiment, the hemoglobin solution is polymerized with glutaraldehyde, and has a methemoglobin content of less than about 15% by weight, an endotoxin concentration less than about 0.5 endotoxin units per ml, and has less than or equal to about 15% by weight polymerized hemoglobin having a molecular weight over about 500,000 Daltons, and less than or equal to about 10% by weight polymerized hemoglobin having a molecular weight less than or equal to about 65,000 Daltons. Optionally, the hemoglobin solution can have an endotoxin content less than about 0.5 endotoxin units per ml.

In one embodiment, the ratio of hemoglobin from the hemoglobin solution to hemoglobin from the stored red blood cells is in a range of between abut 1:9 and about 1:1 by weight. In other embodiments, the ratio of free hemoglobin to cell-associated hemoglobin is about 1:4 or about 2:3 by hemoglobin concentration.

The stored red blood cells and the hemoglobin solution can be administered to the patient in any order. The hemoglobin solution and stored red blood cells can also be administered in an alternating fashion, where a quantity of hemoglobin solution is administered followed by a quantity of stored red blood cells for one or more rounds. In the alternative, the stored red blood cells can be administered first. In one embodiment, the method of the invention includes administering the stored red blood cells within about thirty-six hours of administering the hemoglobin solution. Alternatively, the stored red blood cells are administered within about twenty-four hours, or within eight hours, of administering the hemoglobin solution. In still another embodiment, the stored red blood cells and the hemoglobin solution are administered simultaneously. Preferably, the hemoglobin solution is administered before the stored red blood cells are administered to a patient.

The hemoglobin solution and stored red blood cells can be administered to the patient at any suitable hemoglobin concentration or hematocrit. For example, the hemoglobin solution can be at a concentration of about 10 g/dL. In another embodiment the hemoglobin solution is at a concentration of 14 g/dL. The stored red blood cells can be provided, for example at a hematocrit of about 30 to about 80.

An example of a suitable rate at which the hemoglobin solution, stored red blood cells or combination thereof is administered is in a range of between about 0.5 ml per minute and about 100 ml per minute. In one embodiment, the hemoglobin solution, stored red blood cells or a combination thereof can be administered at a low rate, such as about 2.5 ml per minute. An example of a suitable period of time over which the hemoglobin solution is administered is about 2.5 minutes for about nine (9) hours.

In another embodiment, the invention includes a composition of hemoglobin and stored red blood cells. The composition can be contained in any suitable container for storing or preserving hemoglobin or red blood cells. Preferably, the hemoglobin is polymerized. In a particularly preferred embodiment, the hemoglobin is polymerized with glutaraldehyde.

A method of forming the composition includes combining a suitable hemoglobin solution with suitable stored red blood cells. Suitable hemoglobin solutions and suitable stored blood are as described above. The hemoglobin and stored red blood cells can be combined and then used immediately to treat a patient by the method of the invention, or the combined hemoglobin and red blood cells can be stored for subsequent use.

EXEMPLIFICATION

Preparation of Samples

Fresh red blood cell (Frbc) suspensions were prepared by drawing blood from healthy donors into heparin (0.1 mL/10 mL), chilled to 4° C., centrifuged, and the plasma and buffy coat were removed. The cells were resuspended with two volumes of isotonic phosphate buffered saline (PBS), pH 7.4. Three cycles of centrifugation and resuspension with PBS were performed to remove residual levels of plasma and buffy coat material. The fresh red blood cells were then diluted to 30% hematocrit (hct) and stored at 4° C. until use. If unused for greater than forty eight hours (2 days), the cells were discarded.

Stored red blood cells (Srbc) were essentially packed red cell units purchased from the Gulf Coast Blood Center, Houston, Tex. Standard clinically available units were pulled from the blood bank after a storage time of between four and five weeks. The stored cells were washed with PBS pH 7.4 by repeated centrifugation and resuspension as previously described for fresh red cells. Unlike fresh red cells, there was evidence of hemolysis after the first centrifugation. Washing was repeated until there was no visible hemolysis or cell debris (up to six times). Washed stored red blood cells were diluted to 30% hct and stored at 4° C. until use.

Prior to use in the artificial capillary (FIG. 1) a sample was drawn into a microcapillary hematocrit tube to look for hemolysis and to recheck the hematocrit. Red cell hemoglobin $P_{50}$ was measured with a Hemox analyzer (TCS Medical Products Co., New Hope, Pa.).

The HBOC used in this study was supplied by Biopure Corp., Cambridge, Mass. The HBOC consisted of glutaraldehyde-polymerized, ultrapurified bovine hemoglobin in physiologic solution. The HBOC had a $P_{50}$ of 38 and a Hill coefficient of approximately 1.4. Samples of HBOC were supplied in vacutainers and stored at room temperature until use.

Just prior to use, washed stored red blood cells were mixed with HBOC to make stored red blood cell/HBOC mixtures. There mixtures are designated as "stored red blood cell/HBOC 1-1" and "stored red blood cell/HBOC 9-1." Stored red blood cell/HBOC 1-1 consisted of equal quantities (grams) of erythrocyte hemoglobin (as cells) and cell free hemoglobin (HBOC) corresponding to a final composition of 15% hematocrit and 5 g/dl hemoglobin solution. Stored red blood cell/HBOC 9-1 consisted of 90% red cell hemoglobin (as cells) and 10% cell-free hemoglobin (HBOC) corresponding to a final composition of 27% hematocrit and 1 g/dl hemoglobin solution. Both samples had a total hemoglobin concentration of 10 g/dl.

Experimental System

The experimental apparatus has been previously described, for example, in Page, T. C., et al., "Oxygen Transport by Erythrocyte/Hemoglobin Solution Mixtures in an in Vitro Capillary as a Model of Hemoglobin-Based Oxygen Carrier Performance," *Microvasc. Res.*, 55:54-64 (1998); Page, T. C., et al., "Prediction of Microcirculatory Oxygen Transport by Erythrocyte/Hemoglobin Solution Mixtures," *Microvasc. Res.*, 56:113-126 (1998); and Page, T. C., et al., "Experimental and Mathematical Simulation of Oxygen Transport by Hemoglobin-Based Blood Substitute," *Blood Substitutes—Present and Future Perspectives*, E. Tsuchida (editor) Chapt. 11, pp. 135-145 (1998), the teachings of all of which are incorporated herein in their entirety.

Experimental System

The system includes a silicone rubber capillary film that defines a capillary having a diameter of about 25 μm. Silicone rubber was selected because of its high permeability to oxygen combined with sufficient optical clarity to permit spectroscopic determination of hemoglobin oxygen saturation. The capillary film was mounted on the stage of a microscope. The capillary film was cannulated at each end and perfused with red blood cell suspensions, hemoglobin solutions, or mixtures thereof. A dual wavelength microspectrophotometric method was used to determine the oxygen saturation of the sample at various axial positions along the capillary. Measurements were made at each position along the capillary at known 0% and 100% oxygen saturation. These calibrations were used to calculate the fractional oxygen saturation versus position along the capillary for experimental measurements.

Measurements

For oxygen uptake experiments, samples were deoxygenated in a tonometer and then passed into the feed reservoir through an 8-μm Nucleopore filter. Oxygenated gas was blown over the capillary film while samples were pulled through the capillary lumen. In oxygen release experiments, air-equilibrating samples were pulled through the capillary while the surface of the silicone rubber film was suffused with humidified nitrogen. Samples containing HBOC-301 were equilibrated with 50% oxygen to achieve full saturation (required for calculation of fractional saturation). While in the feed reservoir, samples were continually stirred to prevent sedimentation. Data was taken for four flow rates at five different locations along the capillary. The data was converted to fractional oxygen saturation and presented as fractional saturation versus apparent residence time. The methods by which these calculations were made is discussed in detail in the references identified above with respect to the experimental system employed.

RESULTS

The stored cells required extensive washing and were fragile. The observed $P_{50}$ was 15±1 mmHg as measured by a Hemox Analyzer (TCS Medical Products, New Hope, Pa.). Washed stored red blood cell samples had notable hemolysis after 24 hrs of storage and had to be rewashed.

Oxygen Release

Figure 1:
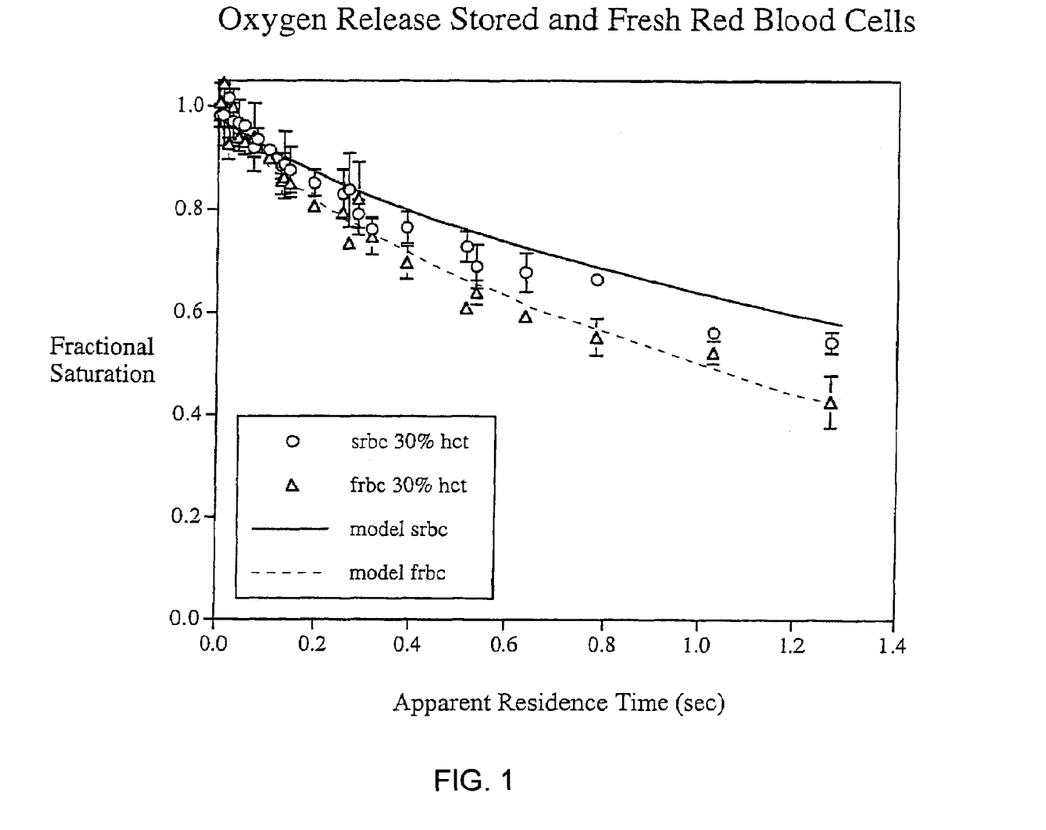
FIG. 1 is a plot of oxygen release over time that compares actual and predicted oxygen release from stored human red blood cells to that of freshly isolated human red blood cells where the points represent experimental data and the curves represent output from a theoretical model.

The results of oxygen transport studies with stored and fresh red blood cells (Srbc and Frbc, respectively, or rbc, generally) are presented in FIG. 1. The data are expressed as the mean±std. dev. These observations were compared with curves predicted by a mathematical model in which the $P_{50}$ was set at 26 mmHg and 15 mmHg for fresh and stored red blood cells, respectively. The hematocrit for these samples was 30%. Oxygen release from the Srbc was significantly reduced in comparison to fresh human red blood cells. The model results agreed with the release data for fresh erythrocytes but slightly under-predicted release from stored erythrocytes.

Figure 2:
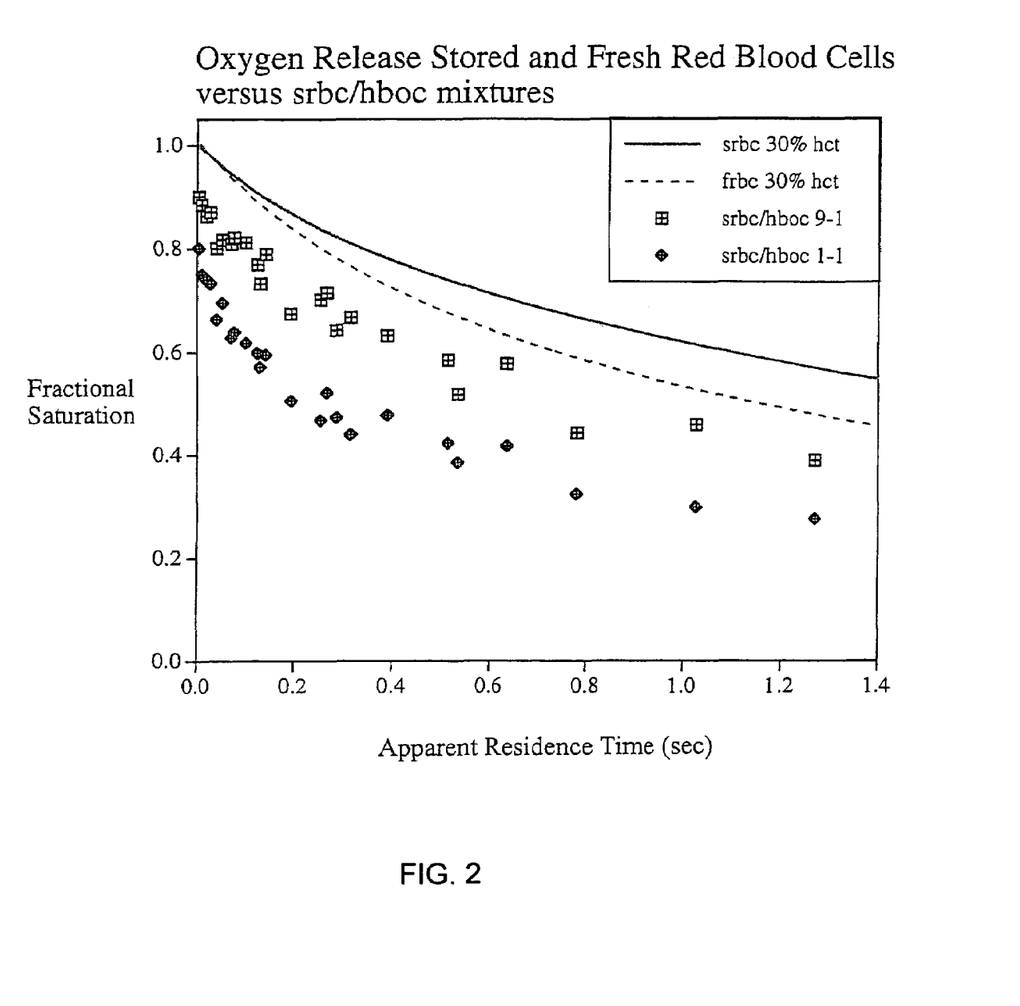
FIG. 2 is a plot of dose response for the effect of addition of hemoglobin-based oxygen carrier (HBOC) to stored red blood cells and to fresh red blood cells on oxygen release.

A summary of release data for a dose response experiment where increasing amounts of HBOC are added to the stored cells is presented in FIG. 2. All samples have been equilibrated with humidified air. Data series for Srbc and Frbc in FIG. 1 are shown as fitted curves for clarity. The equilibrium saturation of the Srbc/HBOC 9-1 samples was calculated to be 0.98 while the equilibrium oxygen saturation of the Srbc/HBOC 1-1 was calculated as 0.92. A substantial increase in oxygen release is noted for even the Srbc/HBOC 9-1 sample, and the efficiency of oxygen release increases at higher fractional concentrations of HBOC. The loss of oxygen transport efficiency resulting from storage is reversed with the addition of a small amount of HBOC.

Figure 3:
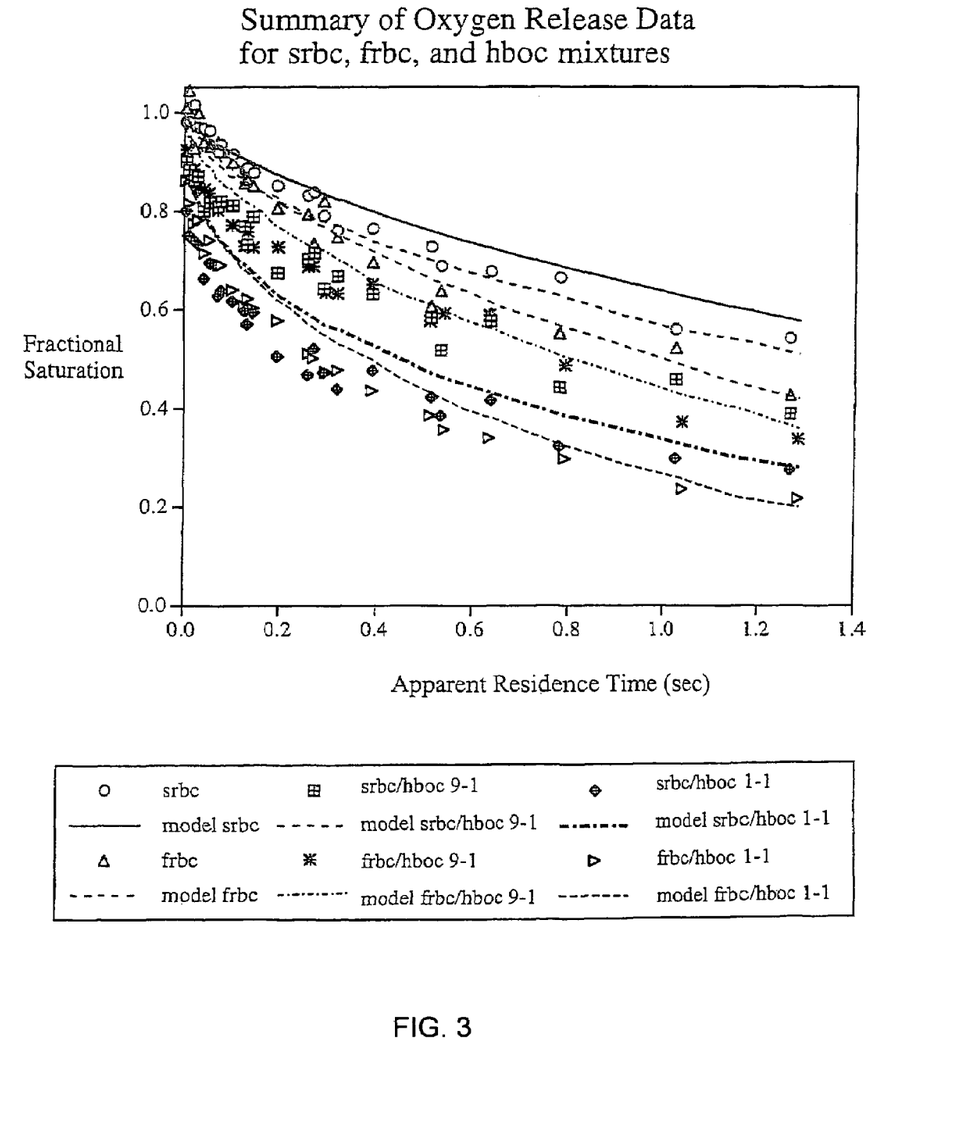
FIG. 3 is a summary of oxygen release over time by samples of fresh red blood cells and stored red blood cells, alone and in combination with two different amounts of a hemoglobin-based oxygen carrier.

A summary of oxygen release by all samples (points) is presented in FIG. 3 with comparison to validated mathematical models (curves) of oxygen transport for red cells and for rbc/HBOC mixtures. As can be seen in FIG. 3, increased oxygen release with addition of HBOC was observed for all Srbc and Frbc mixtures. Samples containing Frbc offloaded more oxygen than the respective samples containing Srbc. The models were predictive for Frbc and Frbc mixtures with HBOC, but for Srbc/HBOC 1-1 and Srbc/HBOC 9-1, the models under-estimated oxygen release for all residence times. Therefore, despite a significantly greater affinity for oxygen, when combined with a hemoglobin-based oxygen carrier, stored red blood cells exhibited a significantly greater rate of release than was predicted. Further, in contrast to predicted behavior, the rate of oxygen release of stored red blood cells is approximately that of fresh red blood cells when mixed with the same amount of hemoglobin-based oxygen carrier.

Oxygen Uptake

Figure 4:
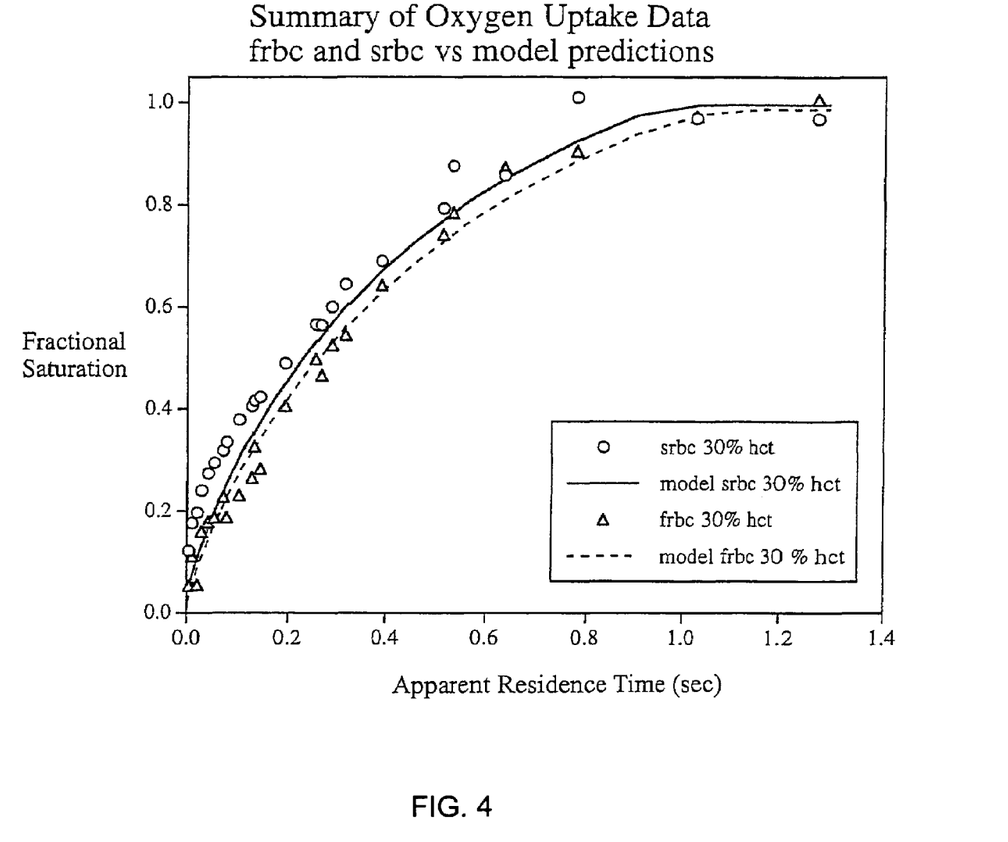
FIG. 4 is a plot of oxygen uptake data for stored and freshly isolated red blood cell suspensions where points represent experimental data and curves represent theoretical simulations.

The results for oxygen uptake by Srbc and Frbc are shown in FIG. 4. The data points were compared with theoretical simulations (curves). The curves were generated by a theoretical red blood cell suspension model. For the fresh cells the $P_{50}$ was set to 26 mmHg and for the stored cells the $P_{50}$ was set to 15 mmHg. Oxygen uptake by the stored cells (circles) was faster than by fresh cells (triangles). The same trends can be seen in the mathematical simulation of the data. The experimental data agree with the theoretical curve for fresh red blood cells, but the experimental data for stored red blood cells showed much higher oxygen uptake rates at short residence times than predicted. This "burst" effect was usually associated with hemoglobin solutions.

Figure 5:
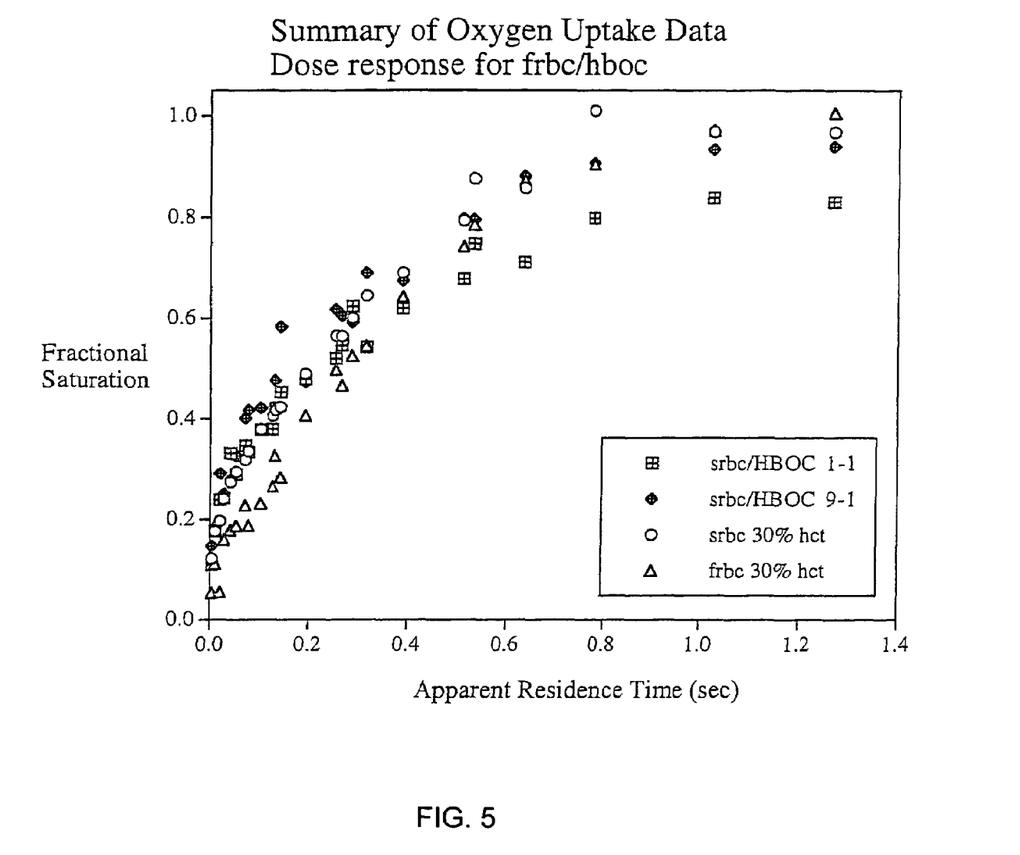
FIG. 5 is a plot of oxygen uptake by stored red blood cells, alone and in combination with a hemoglobin-based oxygen carrier, and by fresh red blood cells alone.

The "burst" effect can be seen in FIG. 5. The results of dose response experiments with Srbc/HBOC mixtures are summarized in FIG. 5 for oxygen uptake. Four data series are presented including Srbc, Srbc/HBOC 1-1, Srbc/HBOC 9-1, and Frbc. The Frbc data series is shown for comparison. Oxygen uptake by Srbc and Srbc/HBOC mixtures was faster than for the Frbc sample. The pure red blood cell samples saturated more fully than the HBOC-containing samples. This was partially due to the reduced oxygen affinity of the HBOC (does not fully saturate with room air). The HBOC-containing samples also approach equilibrium saturation values more slowly than red blood cells alone. This behavior has been previously discussed (Page, et al. (1998), supra). The equilibrium values for rbc/HBOC 1-1 and rbc/HBOC 9-1 are 92 and 98%, respectively. The experimental data series did not reach these saturation levels by 1.3 seconds of retention time.

DISCUSSION

As demonstrated herein, hemoglobin solution restored oxygen transport when added to stored red blood cells, even though the hemoglobin of stored red blood cells had high oxygen affinity. As shown above, addition of hemoglobin solution to stored red blood cells at a ratio of nine parts hemoglobin from stored red blood cells to one part hemoglobin from the hemoglobin solution, by weight, resulted in increased oxygen release over stored red blood cells alone. Oxygen release was restored such that at least as much oxygen was released by the stored red blood cell/hemoglobin solution mixture compared to that released by freshly isolated blood (FIGS. 2 and 3). Addition of HBOC to stored red blood cells at a ratio of a one part hemoglobin from stored red blood cells to one part hemoglobin from HBOC, by weight, resulted in a large increase in oxygen release compared to the 9:1 mixture and compared to fresh red blood cells (FIGS. 2 and 3). This restoration apparently occurred without restoration of 2-3, DPG levels in the stored blood cells.

Oxygen release of the stored red blood cell sample and the stored red blood cell/HBOC 9-1 mixture was higher than predicted by mathematical models (FIG. 3). Red blood cell suspensions were very sensitive to the presence of even small amounts of high affinity, extracellular hemoglobin. Any hemolysis during the experiment resulted in increased extracellular high affinity hemoglobin and a concomitant increase in oxygen release. The red blood cells and the stored red blood cell/HBOC 9-1 mixture were particularly sensitive to this phenomenon, while stored red blood cell/HBOC 1-1 mixtures were less sensitive to small increases in extracellular hemoglobin concentration.

The discrepancy between the model simulations and the experimental data coupled with the observation of free hemoglobin in the withdrawal reservoir during experiments using stored red blood cells indicated that an increased level of extracellular hemoglobin was present due to hemolysis. Although free hemoglobin was present in the stored clinical units due to hemolysis, in the clinical setting, the free hemoglobin would be removed rapidly by the body. For this reason, the level of hemolysis was reduced by cell washing prior to experimental testing. Some hemolysis still occurred during the experiment as evidenced by the presence of free hemoglobin in the withdrawal reservoir.

EQUIVALENTS

The features and other details of the method on the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise specified.

What is claimed is:

1. A method of treating a patient, comprising administering to the patient stored red blood cells and a polymerized hemoglobin solution, wherein the stored red blood cells have been stored for at least about seven days and wherein the stored red blood cells are administered simultaneously with the hemoglobin solution or the hemoglobin solution is administered within about eight hours after the red blood cell administration and the hemoglobin soltuion comprises about 10% to about 50% by weight of total hemoglobin administered to the patient.

2. The method of claim 1, wherein the stored red blood cells have been stored for greater than about thirty-five days.

3. The method of claim 1, wherein the stored red blood cells have been stored for greater than about forty-two days.

4. The method of claim 1, wherein hemoglobin of the stored red blood cells has a $P_{50}$ of less than about 15 mm Hg.

5. The method of claim 1, wherein hemoglobin of the stored red blood cells has a $P_{50}$ of less than about 20 mm Hg.

6. The method of claim 1, wherein the hemoglobin of the stored red blood cells has a $P_{50}$ of less than about 25 mm Hg.

7. The method of claim 1, wherein the hemoglobin is polymerized with glutaraldehyde.

8. The method of claim 1, wherein the polymerized hemoglobin solution has
   a) a methemoglobin content less than about fifteen percent by weight;
   b) an endotoxin concentration less than about 0.5 endotoxin units per milliliter;
   c) less than, or equal to, about fifteen percent by weight polymerized hemoglobin with molecular weight greater than about 500,000 Daltons; and
   d) less than, or equal to, about ten percent by weight polymerized hemoglobin with a molecular weight less than or equal to about 65,000 Daltons.

* * * * *